United States Patent [19]

Drengler

[11] Patent Number: 4,801,456

[45] Date of Patent: Jan. 31, 1989

[54] GROWTH HORMONE-RELEASING FACTOR ANALOGS

[75] Inventor: Keith A. Drengler, Lindenhurst, Ill.

[73] Assignee: International Minerals & Chemical Corp., Terre Haute, Ind.

[21] Appl. No.: 71,351

[22] Filed: Jul. 9, 1987

[51] Int. Cl.$^4$ .......................... A61K 37/43; C07K 7/10
[52] U.S. Cl. ...................................... 424/422; 514/12; 530/324
[58] Field of Search ........................ 530/324; 514/12; 424/422

[56] References Cited

U.S. PATENT DOCUMENTS

| | | | |
|---|---|---|---|
| 4,517,181 | 5/1985 | Ling et al. | 514/12 |
| 4,518,586 | 5/1985 | Rivier et al. | 514/12 |
| 4,528,190 | 7/1985 | Vale, Jr. et al. | 514/12 |
| 4,529,595 | 7/1985 | Rivier et al. | 514/12 |
| 4,562,175 | 12/1985 | Chang et al. | 514/12 |
| 4,563,352 | 1/1986 | Rivier et al. | 514/12 |
| 4,585,756 | 3/1986 | Brazeau, Jr. et al. | 514/12 |
| 4,595,676 | 6/1986 | Spiess et al. | 514/12 |
| 4,605,643 | 8/1986 | Bohlen et al. | 514/12 |
| 4,610,976 | 9/1986 | Bohlen et al. | 514/12 |
| 4,617,149 | 10/1986 | DiMarchi et al. | 530/324 |
| 4,622,312 | 11/1986 | Felix et al. | 514/12 |
| 4,626,523 | 12/1986 | Vale, Jr. et al. | 514/12 |
| 4,628,043 | 12/1986 | Spiess et al. | 514/12 |
| 4,649,131 | 3/1987 | Felix et al. | 514/12 |
| 4,659,693 | 4/1987 | Nestor | 530/324 |

FOREIGN PATENT DOCUMENTS

| | | |
|---|---|---|
| 0136475 | 4/1985 | European Pat. Off. |
| 0138416 | 4/1985 | European Pat. Off. |

OTHER PUBLICATIONS

Robberecht et al., Chem. Abstr., vol. 106, No. 691h (1987).

Lance et al., Super-Active Analogs of Growth Hormone-Releasing Factor, Biochemical and Biophysical Research Communication, vol. 119, No. 1, pp. 265-272 (1984).

Wehrenberg and Ling, In vivo Biological Potency of Rat and Human Growth Hormone-Releasing Factor and Fragments of Human Growth Hormone-Releasing Factor, Biochemical and Biophysical Research Communication, vol. 115, No. 2, pp. 525-530 (1983).

Ling et al., Synthesis and In vitro Bioactivity of Human Growth Hormone-Releasing Factor Analogs Substituted at Position-1, Biochemical and Biophysical Research Communication, vol. 122, No. 1, pp. 304-310 (1984).

Ling et al., Synthesis and In vitro Bioactivity of C-Terminal Deleted Analogs of Human Growth Hormone-Releasing Factor, Biochemical and Biophysical Research Communication, vol. 123, No. 2, pp. 854-861 (1984).

Coy et al., Structure-Activity Studies on the N-Terminal Region of Growth Hormone Releasing Factor, J. Med. Chem., 28,181 (1985).

*Primary Examiner*—Delbert R. Phillips
*Assistant Examiner*—Christina Chan
*Attorney, Agent, or Firm*—Wendell Ray Guffey; Thomas L. Farquer

[57] ABSTRACT

Human Growth Hormone-Releasing Factor (hGRF) analogs having the sequence $[X^3, Y^8, Z^{25}, Nle^{27}]$-hGRF(1-A)—B, wherein X, Y, and Z are selected from the group consisting of Asn and Asp, A has a value from 29-44, and B is $NH_2$ or OH are synthesized and administered to animals to stimulate the release of Growth Hormone (GH).

15 Claims, No Drawings

GROWTH HORMONE-RELEASING FACTOR ANALOGS

This invention relates generally to human growth hormone-releasing factor (hGRF) analogs and particularly to hGRF analogs having the sequence: [$X^3$, $Y^8$, $Z^{25}$, $Nle^{27}$]- hGRF(1-A)-B, wherein X, Y, and Z are selected from the group consisting of Asn and Asp, A has a value from 29-44, and B is $NH_2$ or OH.

BACKGROUND OF THE INVENTION

Human Growth hormone-releasing Factor (hGRF) is a 44 amino acid peptide having growth hormone (GH) releasing activity as reported by Guillemin et al., 218, Science 585 (1982). hGRF is usually isolated from pancreatic human tumor cells (hpGRF). hpGRF has the structure H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Gln-Gln-Gly-Glu-Ser-Asn-Gln-Glu-Arg-Gly-Ala-Arg-Ala-Arg-Leu-$NH_2$. Since the initial discovery of hGRF, several peptides, designated herein as analogs, having deleted, substituted or otherwise modified sequences have been reported to have GH releasing activity. Rivier et al., 300 Nature 276 (1982) reported a peptide that terminates as a free carboxylic acid and differs from hGRF by the absence of the C-terminal tetrapeptide amide -Arg-Ala-Arg-Leu-$NH_2$. Rivier et al. tested a number of shortened GRF analogs and reported that, when compared in vitro with the parent hpGRF(1-40)—OH, the following analogs exhibited similar activity: hpGRF(1-29)—$NH_2$, hpGRF(1-32)—$NH_2$, hpGRF(1-39)—$NH_2$, hpGRF(1-40)—$NH_2$, and hpGRF(1-27)—$NH_2$.

Numerous synthetic GRF peptides and GRF analogs have been patented: U.S. Pat. No. 4,610,976 to Bohlen discloses 44 amino acid synthetic peptides described as extremely potent in stimulating the release of pituitary GH in mammals. These synthetic peptides, biologically active fragments thereof, analogs thereof, or nontoxic salts thereof can be dispersed in a pharmaceutically acceptable carrier and administered for diagnostic or therapeutic purposes. The 44 amino acid polypeptide is believed to be porcine GRF. U.S. Pat. No. 4,605,643 to Bohlen discloses a 44 amino acid synthetic polypeptide that is the replicate of the native GRF of the sheep hypothalmus. The peptide is extremely potent in stimulating the release of GH in mammals. The patent states that the peptide, biologically active fragments thereof, analogs thereof, or nontoxic salts thereof may be administered to animals for therapeutic or diagnostic purposes. As examples of biologically active fragments, Bohlen states that fragments 34-43 residues in length, or even shorter fragments, e.g. oGRF (1-32), that retain an —OH or —$NH_2$ of the C-terminal and retain the desired biological activity are suitable. U.S. Pat. No. 4,595,676 to Spiess discloses the synthesis of rat hypothalamic GRF. A number of polypeptides, which have 44 amino acids, and are useful in stimulating the release of GH in animals are disclosed. Reference also is made to biologically active fragments of the polypeptides. U.S. Pat. No. 4,585,756 to Brazeau discloses a 44-residue polypeptide isolated from purified extracts of bovine hypothalami and useful for promoting the growth of animals. Reference is made to biologically active fragments thereof, including bGRF(1-40) and bGRF (1-37) or shorter fragments. U.S. Pat. No. 4,563,352 to Rivier describes the synthesis of human pancreatic GRF and biologically active fragments thereof and provides synthetic peptides useful in stimulating the release of pituitary GH in mammals. U.S. Pat. No. 4,562,175 to Chang discloses a synthetic peptide GRF useful in growth inducing pharmaceutical compositions. The peptide is based on the structure of human pancreatic GRF. The synthetic peptide differs from the natural peptide by comprising norleucine in place of methionine at position 27. Other analogous peptides susceptible to a similar modification also are disclosed, including [D-$Ala^2$, $Nle^{27}$]-hpGRF(1-44)—$NH_2$ and [D-$Ala^2$, $Nle^{27}$]-ratGRF(1-43)—$NH_2$). U.S. Pat. No. 4,529,595 to Rivier discloses analogs of hpGRF useful in stimulating the release of pituitary GH in mammals. Biologically active fragments, said to generally extend from the N-terminal to a residue between positions 27 and 32, also are disclosed. U.S. Pat. No. 4,528,190 to Vale provides synthetic polypeptides, useful in stimulating the release of pituitary GH in animals, which have resistance to enzymatic degradation in the body. U.S. Pat. No. 4,518,586 to Rivier describes a 44-amino acid synthetic polypeptide in which any or all of the residues between the 29th and 44th residues may be deleted. U.S. Pat. No. 4,517,181 to Ling discloses synthetic porcine GRF peptides which promote the release of GH by the pituitary gland and teaches that deletions can be made beginning at the carboxyl end of the peptide to create fragments that retain substantial portions of the potency of the peptide. U.S. Pat. No. 4,617,149 discloses a class of 44-amino acid polypeptide analogs of hpGRF bearing substitutions of the amino acid at position 27. Other similar GRF analogs are disclosed in U.S. Pat. Nos. 4,622,312 and 4,626,523.

Similarly, there have been many publications relating to GRF analogs: Ling et al., Synthesis and In Vitro Bioactivity of C-Terminal Deleted Analogs of Human Growth Hormone-Releasing Factor, Biochem. Biophys. Res. Commun., 123(2), 854-861 (1984); Ling et al., Synthesis and In Vitro Bioactivity Human Growth Hormone-Releasing Factor Analogs Substituted at Position-1, Biochem. Biophys. Res. Commun., 122(1), 304-310 (1984); Wehrenberg et al., In Vitro Biological Potency of Rat and Fragments, Biochem. Biophys. Res. Commun., 115(2), 525-530 (1984); Coy et al., Structure-Activity Studies on the N-Terminal Region of, J. Med. Chem., 28, 181-185 (1985); and Lance et al., Super-Active Analogs (1-29)-Amide, Biochem. Biophys. Res. Commun., 119(1), 265-272 (1984).

Although numerous patents and publications relating to GRF analogs have been disclosed in the prior art, there exists a continuing need for synthetic GRF analogs which stimulate the release of GH and induce the beneficial effects associated therewith.

SUMMARY OF THE INVENTION

It is, therefore, an object of the present invention to provide human growth hormone-releasing factor (hGRF) analogs.

It is another object of the present invention to provide hGRF analogs which stimulate the release of pituitary growth hormone (GH) in animals.

It is another object of the present invention to provide hGRF analogs having substitutions at positions 3, 8, 25, and 27.

It is another object of the present invention to provide hGRF analogs having various combinations of Asn and Asp at positions 3, 8, and 25.

It is a further object of the present invention to provide a composition containing the hGRF analogs of the present invention suitable for administration to animals to stimulate the release of pituitary GH.

These and other objects are achieved by synthesizing hGRF analogs having the sequence [X$^3$, Y$^8$, Z$^{25}$, Nle$^{27}$]-hGRF(1-A)—B, wherein X, Y, and Z are selected from the group consisting of Asn and Asp, A has a value from 29–44, and B is NH$_2$ or OH, and administering the hGRF analogs to animals to stimulate the release of GH and induce the beneficial effects of increased GH levels.

In the preferred embodiment, hGRF analogs having the sequence [X$^3$, Y$^8$, Z$^{25}$, Nle$^{27}$]- hGRF(1-31)—NH$_2$, wherein X, Y, and Z are selected from the group consisting of Asn and Asp, are synthesized and administered to animals to stimulate the release of GH and induce the beneficial effects of increased GH levels.

Other objects, advantages, and novel features of the present invention will become apparent from the following detailed description of the invention.

DETAILED DESCRIPTION OF THE INVENTION

The amino acids referred to herein are described by shorthand designations as follows:

| Amino Acid Nomenclature | | |
|---|---|---|
| Name | 3-letter | 1-letter |
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met(O) | — |
| Methionine methylsulfonium | Met(S—Me) | — |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

To simplify the nomenclature used to disclose the peptide sequences of the present invention, the following well-known shorthand notation wil be used herein: [X$^3$, Y$^8$, Z$^{25}$, Nle$^{27}$]-hGRF(1-A)—B, wherein the (1-A) indicates that the peptide has the same sequence as the first A amino acids of the original 44-residue hGRF; except for the amino acids at positions 3, 8, 25, and 27 which have been replaced by amino acids designated X, Y, Z, and Nle, respectively. For example, [Asn$^3$, Asp$^8$, Asn$^{25}$, Nle$^{27}$]-hGRF(1-31)—NH$_2$ indicates a peptide 31 amino acids long whose sequence is the same as the first 31 amino acids of native hGRF except that Nle has been substituted for Met at position 27, Asn has been substituted at position 25, Asp has been substituted at position 8, and Asn has been substituted at position 3 when read from the amino terminal end of native GRF. The complete sequence, expressed using the 3 letter code, for this amino acid would therefore be H-Tyr-Ala-Asn-Ala-Ile-Phe-Thr-Asp-Ser-Tyr-Arg-Lys-Val-Leu-Gly-Gln-Leu-Ser-Ala-Arg-Lys-Leu-Leu-Gln-Asn-Ile-Nle-Ser-Arg-Gln-Gln-NH$_2$. Similarly, [Asn$^3$, Nle$^{27}$]-hGRF(1-31)—NH$_2$ indicates a peptide 31 amino acids long, whose sequence is the same as the first 31 amino acids of native hGRF except that Nle has been substituted for Met at position 27 and Asn has been substituted at position 3.

According to the present invention, human growth hormone-releasing factor (hGRF) analogs having the sequence [X$^3$, Y$^8$, Z$^{25}$, Nle$^{27}$]-hGRF(1-A)—B, wherein X, Y, and Z are selected from the group consisting of Asn and Asp, A has a value from 29–44, and B is NH$_2$ or OH, are synthesized and used to stimulate the release of growth hormone (GH) in animals. The hGRF analogs of the present invention are peptides having the general sequence of hGRF but differing therefrom by the deletion of 44 minus A amino acids from the amino terminal end, by replacement of native amino acids at positions 3, 8, 25 by Asn and Asp, by replacement of the methionine residue at position 27 with norleucine (Nle), and by replacement of NH$_2$ by OH for some of the hGRF analogs. Obviously, GRF analogs wherein X, Y, and Z correspond to the native sequence, Asp, Asn, and Asp respectively, are not included within the scope of the present invention.

Preferably, the hGRF analogs of the present invention have the sequence [X$^3$, Y$^8$, Z$^{25}$, Nle$^{27}$]-hGRF(1-31-)—NH$_2$, wherein X, Y, and Z are selected from the group consisting of Asn and Asp. The sequence for the preferred hGRF analogs of the present invention expressed using the 3 letter code for the amino acid is: H-Tyr-Ala-X-Ala-Ile-Phe-Thr-Y-Ser-Tyr-Arg-Lys-Val-Leu-Gly-Gln-Leu-Ser-Ala-Arg-Lys-Leu-Leu-Gln-Z-Ile-Nle-Ser-Arg-Gln-Gln-NH$_2$, wherein X, Y, and Z are defined as above.

The following peptide sequences, using the shorthand notation, depict examples of the hGRF analogs of the present invention:

[Asn$^3$, Nle$^{27}$]-hGRF(1-31)—NH$_2$;
[Asp$^8$, Nle$^{27}$]-hGRF(1-31)—NH$_2$;
[Asn$^{25}$, Nle$^{27}$]-hGRF(1-31)—NH$_2$;
[Asn$^3$, Asn$^{25}$, Nle$^{27}$]-hGRF(1-31)—NH$_2$;
[Asp$^8$, Asn$^{25}$, Nle$^{27}$]-hGRF(1-31)—NH$_2$;
[Asn$^3$, Asp$^8$, Nle$^{27}$]-hGRF(1-31)—NH$_2$; and
[Asn$^3$, Asp$^8$, Asn$^{25}$, Nle$^{27}$]-hGRF(1-31)—NH$_2$.

Each of the hGRF analogs of the present invention are defined to include pharmaceutically acceptable non-toxic acid addition salts and/or a pharmaceutically acceptable non-toxic carbolated acid salts.

The term "pharmaceutically acceptable non-toxic acid addition salts" encompasses both organic and inorganic acid addition salts including, for example, those prepared from acids such as hydrochloric, hydrofluoric, sulfuric, sulfonic, tartaric, fumaric, hydrobromic, glycolic, citric, maleic, phosphoric, succinic, acetic, nitric, benzoic, ascorbic, p-toluenesulfonic, benzenesulfonic, naphthalenesulfonic, propionic, and the like. Preferably, the acid addition salts are those prepared from hydrochloric acid, acetic acid, or succinic acid. Any of the above salts is prepared by conventional methods well known to skilled artisans.

The term "carbolated acid salts" includes, for example, ammonium, alkali metal salts such as sodium, potassium, and lithium, and the like.

The hGRF analogs of the present invention can be synthesized by any of a variety of recognized peptide synthesis techniques including classical (solution) methods and solid phase methods, with solid phase synthesis being preferred.

Solid phase techniques in which the C-terminal amino acid of the sequence is attached to an insoluble support followed by sequential addition of the remaining amino acids in the sequence is the preferred method for preparing the hGRF analogs of the present invention. Techniques for solid phase synthesis are described by Barany and Merrifield, Solid-Phase Peptide Synthesis; In "The Peptides: Analysis, Synthesis, Biology. Volume 2: Special Methods in Peptide Synthesis, Part A"; Gross and Meienhofer, J. Eds.; Academic Press: New York, 1980; pp. 3-284:and J. Stewart et al., Solid Phase Peptide Synthesis, 2nd Edition, Pierce Chemical Co., Rockford, IL 1984.

Solid phase synthesis is commenced from the C-terminal end of the peptide by coupling a protected amino acid to a suitable resin. A starting material can be prepared by attaching an amino-protected amino acid via a benzyl ester linkage to a chloromethylated resin or a hydroxymethyl resin or via an amide bond to a benzhydrylamine (BHA) resin or p-methylbenzhydrylamine (MBHA) resin. The resins are available commercially and their preparation is known by one of ordinary skill in the art.

The acid form of peptides may be prepared by the solid phase peptide synthesis procedure using a benzyl ester resin as a solid support. The corresponding amides may be produced by using benzhydrylamine or methylbenzhydrylamine resin as the solid support for solid phase peptide synthesis. Those skilled in the art will recognize that when the BHA or MBHA resin is used, treatment with anhydrous HF to remove the polypeptide from the solid support results in a polypeptide having a terminal amide group.

It should be reooqnized that the -amino group of each amino acid employed in the peptide synthesis must be protected during the coupling reaction to prevent side reactions involving the reactive -amino function. It should also be recognized that certain amino acids contain reactive side-chain functional groups (e.g. sulfhydryl, amino, carboxyl, and hydroxyl), and that such functional groups must also be protected with suitable protecting groups which will prevent a chemical reactions from occurring at that site both during the initial and subsequent coupling steps. Suitable protecting groups, known in the art, are described in E. Gross & J. Meienhofer, The Peptides: Analysis, Synthesis, Biology, Volume 3: Protection of Functional Groups in Peptide Synthesis, Academic Press, New York, N.Y., 1981.

In selecting a particular protecting group, certain conditions must be observed. An α-amino protecting group (1) must render the α-amino function inert under the conditions employed in the coupling reaction, (2) must be readily removable after the coupling reaction under conditions that will not remove side chain protecting groups and will not alter the structure of the peptide fragment, and (3) must eliminate the possibility of racemization upon activation immediately prior to coupling. A side chain protecting group (1) must render the side chain functional group inert under the conditions employed in the coupling reaction, (2) must be stable under the conditions employed in removing the α-amino protecting group, and (3) must be readily removable upon completion of the desired amino acid sequence under reaction conditions that will not alter the structure of the peptide chain.

It will be apparent to those skilled in the art that the protecting groups known to be useful for peptide synthesis will vary in reactivity to the agents employed for their removal. For example, certain protecting groups, such as triphenylmethyl and 2-(p-biphenylyl)isopropyloxycarbonyl are very labile and can be cleaved under mild acid conditions. Other protecting groups, such as t-butyloxycarbonyl (Boc), t-amyloxycarbonyl, adamantyloxycarbonyl, and p-methoxybenzyloxycarbonyl, are less labile and require moderately strong acids, such as trifluoroacetic, hydrochloric, or boron trifluoride in acetic acid, for their removal. Still other protecting groups, such as benzyloxycarbonyl (Cbz or Z), halobenzyloxycarbonyl, p-nitrobenzyloxycarbonyl, cycloalkyloxycarbonyl, and isopropyloxycarbonyl, are even less labile and require stronger acids, such as hydrogen fluoride, hydrogen bromide, or boron trifluoroacetate in trifluoroacetic acid, for their removal.

Illustrative examples of amino acid protecting groups include: (1) For an α-amino group, protection may include (a) aromatic urethane-type groups, such as fluorenylmethyloxycarbonyl (Fmoc), Cbz, and substituted benzyloxycarbonyl, such as, for example, p-chlorobenzyloxycarbonyl, p-bromobenzyloxycarbonyl, p-nitrobenzyloxycarbonyl, and p-methoxybenzyloxycarbonyl, o-chlorobenzyloxycarbonyl, 2,4-dichlorobenzyloxycarbonyl, 2,6-dichlorobenzyloxycarbonyl, and the like; (b) aliphatic urethane-type groups such as Boc, t-amyloxycarbonyl, isopropyloxycarbonyl, 2-(p-biphenylyl)isopropyloxycarbonyl, allyloxycarbonyl, and the like; (c) cycloalkyl urethane-type groups such as cyclopentyloxycarbonyl, cyclohexyloxycarbonyl, cycloheptyloxycarbonyl, adamantyloxycarbonyl, and the like. The preferred α-amino protecting group is t-butyloxycarbonyl (Boc).

(2) For the side chain amino group present in Lys, protection may be by any of the groups mentioned hereinabove for protection of an α-amino group. Typical groups include, for example, Boc, p-chlorobenzyloxycarbonyl, p-bromobenzyloxycarbonyl, o-chlorobenzyloxycarbonyl (2-ClZ), 2,6-dichlorobenzyloxycarbonyl, 2,4-dichlorobenzyloxycarbonyl, o-bromobenzyloxycarbonyl, p-nitrobenzyloxycarbonyl t-butyloxycarbonyl, isopropyloxycarbonyl, t-amyloxycarbonyl, cyclopentyloxycarbonyl, cyclohexyloxycarbonyl, cycloheptyloxycarbonyl, adamantyloxycarbonyl, p-toluenesulfonyl, and the like. The preferred side chain amino protecting group is o-chlorobenzyloxycarbonyl (2-ClZ).

(3) For the guanidino group of Arg, protection may be by nitro, tosyl (Tos), Cbz, adamantyloxycarbonyl, and Boc. The preferred protecting group is Tos.

(4) For the hydroxyl group of Ser, Thr, or Tyr, protection may be, for example, by $C_1$–$C_4$ alkyl, such as methyl, ethyl, and t-butyl; benzyl (Bzl); substituted benzyl, such as p-methoxybenzyl, p-nitrobenzyl, p-chlorobenzyl, o-chlorobenzyl, and 2,6-dichlorobenzyl. The preferred aliphatic hydroxyl protecting group for Ser and Thr is benzyl (Bzl), while the Tyr aromatic hydroxyl is most commonly protected as the 2,6-dichlorobenzyl ether ($Cl_2$-Bzl).

(5) For the carboxyl group of Asp or Glu, protection may be, for example, by esterification using groups such as benzyl, t-butyl, cyclohexyl, cyclopentyl, and the like.

The preferred groups are benzyl (Bzl) and cyclohexyl (cHex).

The amino acids are coupled to the peptide chain using techniques well-known in the art for the formation of peptide bonds. One method involves converting the amino acid to a derivative that will render the carboxyl group more susceptible to reaction with the free N-terminal amino group of the peptide fragment. For example, the amino acid can be converted to a mixed anhydride by reaction of a protected amino acid with ethyl chloroformate, phenyl chloroformate, sec-butyl chloroformate, isobutyl chloroformate, pivaloyl chloride, or like acid chlorides. Alternatively, the amino acid can be converted to an active ester such as a 2,4,5-trichlorophenyl ester, a pentachlorophenyl ester, a p-nitrophenyl ester, a N-hydroxysuccinimide ester, or an ester formed from 1-hydroxybenzotriazole.

Another coupling method involves use of a suitable coupling agent such as N,N'-dicyclohexylcarbodiimide (DCC) or N,N'-diisopropylcarbodiimide (DIPCDI). Other appropriate coupling agents, apparent to those skilled in the art, are disclosed in E. Gross & J. Meienhofer, The Peptides: Analysis, Structure, Biology. Vol.1: Major Methods of Peptide Bond Formation, Academic Press, New York, 1979.

The C-terminal amino acid, e.g. Gln, is protected at the N-amino position by an appropriately selected protecting group, in the case of Gln by t-butyloxycarbonyl (Boc). The Boc-Gln-OH can be first coupled to the benzhydrylamine resin using isopropylcarbodiimide at about 25° C. for 2 hours with stirring. Following the coupling of the Boc protected amino acid to the resin support, the α-amino protecting group is removed, using trifluoroacetic acid (TFA) in methylene chloride or TFA alone. The deprotection is carried out at a temperature between about 0° C. and room temperature.

After removal of the α-amino protecting group, the remaining Boc-protected amino acids are coupled stepwise in the desired order or as an alternative to adding each amino acid separately in the synthesis, some may be coupled to one another prior to addition to the solid phase synthesizer. The selection of an appropriate coupling reagent is known to one of ordinary skill in the art. Particularly suitable is diisopropylcarbodiimide (DIPCDI).

Each protected amino acid or amino acid sequence is introduced into the solid phase reactor in excess, and the coupling may be carried out in a medium of dimethylformamide (DMF) or methylene chloride ($CH_2Cl_2$) or mixtures thereof. In cases where incomplete coupling occurs, the coupling procedure is repeated before removal of the N-amino protecting group prior to the coupling of the next amino acid. The success of the coupling reaction at each stage of synthesis may be monitored. A preferred method of monitoring the synthesis is by the ninhydrin reaction. The coupling reactions can be performed automatically using well known methods, for example using a Biosearch 9500 Peptide Synthesizer.

Cleavage of the peptide from the resin can be effected using procedures well known in peptide chemistry. Reaction with hydrogen fluoride in the presence of anisole and dimethylsulfide at 0° for 1 hour will simultaneously remove the side chain protecting groups and release the peptide from the resin.

Purification of the polypeptides of the invention can be effected using procedures well known in peptide chemistry. The subject polypeptides may be purified using preparative HPLC; however, other known chromatographic procedures well known to skilled artisans such as gel permeation, ion exchange and partition chromatography or countercurrent distribution can also be employed.

The hGRF analogs of the present invention stimulate the release of GH and therefore have many uses. The present compounds may be used, for example, in treating primary dwarfism; short stature; wound healing; bone wasting diseases, such as osteoporosis; general catabolic states due to illness, trauma, or surgery; fracture healing; and the like. In addition, the hGRF analogs of the present invention may be used to promote growth in animals such as cattle, swine, sheep, poultry, and the like.

According to the present invention, a method for stimulating the release of GH in animals comprises administering to the animals an amount of the hGRF analogs of the present invention sufficient to stimulate the release of GH.

The hGRF analogs of the present invention can be administered as the compound or as a pharmaceutically acceptable salt of the compound. The hGRF analogs can be administered alone, in combination, or in combination with pharmaceutically acceptable carriers such as various diluents and vehicles. The carrier can be any biocompatible and hGRF compatible carrier. Most preferably, the hGRF analogs are mixed individually or in combination with pharmaceutically acceptable carriers to form compositions which allows for easy dosage preparation.

Doses of the hGRF analogs of the present invention are administered to the recipient for a period during which stimulation of the release of GH is desired. The amount of hGRF analog administered may vary depending upon the particular type of animal, the maturity of the animal, the size of the animal, and whether the dose is to act therapeutically or prophylactically. Generally, the hGRF analogs are administered to the animal according to the present invention in dosages from about 0.05–100 μg/kg of body weight/day (μg/kg/day), preferably from about 0.5–50 μg/kg/day.

The hGRF analogs according to the present invention can be administered to the animals in any acceptable manner including nasally, orally, by injection, using an implant, and the like. Injections and implants are preferred because they permit precise control of the timing and dosage levels used for administration. The hGRF analogs according to the present invention are preferably administered parenterally. As used herein, parenteral administration means administration by intravenous, intramuscular, subcutaneous, or intraperitoneal injection, or by subcutaneous implant.

When administering the hGRF analogs of the present invention parenterally, the pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example glycerol, propylene glycol, liquid polyethylene glycol, and the like), suitable mixtures thereof, and vegetable oils. Proper fluidity can be maintained, for example, by the use of a coating such as lecithin, by the maintenance of the required particle size in the case of dispersion and by the use of surfactants. Nonaqueous vehicles such as cottonseed oil, sesame oil, olive oil, soybean oil, corn oil, sunflower oil, or peanut oil and esters such as isopropyl myristate may also be used as solvent systems for compound compositions. Additionally, various additives which enhance the stability, sterility, and isotonicity of the composition including antimicrobial preservatives, antioxidants, chelating agents, and buffers can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. Any vehicle, diluent, or additive used would, however, have to be compatible with the compounds according to the present invention.

Sterile injectable solutions can be prepared by incorporating the hGRF analogs of the present invention in the required amount of the appropriate solvent with various of the other ingredients, as desired.

The hGRF analogs can be administered to the animals in an injectable formulation containing any biocompatible and compound compatible carrier such as various vehicles, adjuvants, additives, and diluents.

The hGRF analogs are added to the carrier in amounts sufficient to supply from about 0.05–100 μg/kg/day to the animal when injected. Preferably, the hGRF analogs are added to the carrier in amounts sufficient to supply from about 0.5–50 μg/kg/day to the animal.

The hGRF analogs according to the present invention can be administered parenterally to the animals in the form of slow-release subcutaneous implants or targeted delivery systems such as polymer matrices, liposomes, and microspheres. An implant suitable for use in the present invention can take the form of a pellet which slowly dissolves after being implanted or a biocompatible and animal compatible delivery module well known to those skilled in the art. Such well known dosage forms and modules are designed such that the active ingredients are slowly released over a period of several days to several weeks. Examples of well known implants and modules useful in the present invention include: U.S. Pat. No. 4,487,603 discloses an implantable micro-infusion pump for dispensing medication at a controlled rate. U.S. Pat. No. 4,486,194 discloses a therapeutic device for administering medicants through the skin. U.S. Pat. No. 4,447,233 discloses a medication infusion pump for delivering medication at a precise infusion rate. U.S. Pat. No. 4,447,224 discloses a variable flow implantable infusion apparatus for continuous drug delivery. U.S. Pat. No. 4,439,196 discloses an osmotic drug delivery system having multi-chamber compartments. U.S. Pat. No. 4,475,196 discloses an osmotic drug delivery system. These patents are incorporated herein by reference. Many other such implants, delivery systems, and modules are well known to those skilled in the art.

The implant, pellet, module, or other similar delivery system according to the present invention is designed to deliver the hGRF analogs in amounts from about 0.05–100 μg/kg/day, preferably from about 0.5–50 μg/kg/day.

The hGRF analogs according to the present invention can be administered orally to the animal. Conventional methods such as administering the compounds in tablets, suspensions, solutions, emulsions, capsules, powders, syrups, feed compositions, and the like are usable but not preferred since the biological activity of the peptide is often destroyed in the stomach. Known techniques which deliver the peptide orally and retain the biological activity of the peptide are preferred.

According to the present invention, one composition for stimulating the release of GH in animals comprises a pharmaceutically acceptable carrier and an amount of a hGRF analog sufficient to stimulate the release of GH admixed with the carrier. The composition of the present invention contains the hGRF analogs in amounts sufficient to supply from about 0.05–100 μg/kg of body weight/day (μg/kg/day), preferably from about 0.5–50 μg/kg/day.

The composition can be in a form suitable for parenteral administration, typically suspensions, solutions, emulsions, injectable formulations, implants, and the like.

The hGRF analogs according to the present invention can be administered to the animals in a composition comprising an implant or injectable formulation containing any biocompatible and hGRF analog compatible carrier such as various vehicles, adjuvants, additives, and diluents.

Preferably, the composition according to the present invention is (1) an implant pellet comprising a biocompatible and hGRF analogs-compatible implant material and an amount of the hGRF analog sufficient to stimulate the release of GH, or (2) an injectable formulation comprising a biocompatible and hGRF analogs-compatible carrier and an amount of the hGRF analog sufficient to stimulate the release of GH.

It is especially advantageous to formulate the hGRF analogs of the present invention in unit dosage form for ease of administration and uniformity of dosage. Unit dosage form as used herein refers to a physically discrete units suited as unitary dosages for the subject to be treated. Each unit contains a predetermined quantity of the compound calculated to produce the desired therapeutic effect in association with the pharmaceutically acceptable carrier. The specific unit dosage form is dictated by and directly dependent upon (a) the unique characteristics of the particular composition and (b) the particular therapeutic or prophylactic effect to be achieved.

Any animal species in need of prophylactic or therapeutic treatment using GH can be administered the hGRF analogs and compositions according to the present invention. Human, bovine, porcine, canine, feline, equine, avian, and ovine are preferred, with livestock and poultry such as cattle, swine, sheep, chickens, and turkeys being most preferred.

The invention having been generally described, the following examples are given as particular embodiments of the invention and to demonstrate the practice and advantages thereof. It is understood that the examples are given by way of illustration and are not intended to limit the specification or the claims to follow in any manner.

The following abbreviations are used in examples to indicate various protecting groups and reagents; Boc=t-butyloxycarbonyl, Z=benzyloxycarbonyl, 2-ClZ=2-chlorobenzyloxycarbonyl, Bzl=benzyl, $C_{12}$-Bzl=2,6-dichlorobenzyl, Tos=p-toluenesulfonyl, DIPCDI=diisopropylcarbodiimide, MBHA=p-methylbenzhydrylamine, DMF=dimethylformamide, TFA=trifluoroacetic acid, $CH_2Cl_2$=methylene chloride, and DIPEA=diisopropylethylamine.

The analogs of this invention were prepared by sequential coupling of amino acids using a commercially available automated solid phase peptide synthesizer (Biosearch 9500 Peptide Synthesizer). N$\alpha$-Boc-amino acids were used in the synthesis.

Trifunctional amino acids were protected as N$\alpha$-Boc-Lys(2-ClZ), N$\alpha$-Boc-Asp(Bzl), N$\alpha$-Boc-Glu(Bzl), N$\alpha$-Boc-Ser(Bzl), N$\alpha$-Boc-Thr(Bzl), N$\alpha$-Boc-Tyr(Cl$_2$-Bzl) and N-Boc-Arg(Tos). Protected amino acids can be purchased from Biosearch, Peptides International, Peninsula Laboratories, or Bachem.

EXAMPLE 1

Preparation of [Asn$^3$, Nle$^{27}$]-hGRF(1–31)—NH$_2$

The synthesis of [Asn$^3$, Nle$^{27}$]-hGRF(1–31)—NH$_2$ is conducted in a stepwise manner using classical solid phase techniques (Barany, G.; Merrifield, R. B. Solid-Phase Peptide Synthesis. In "The Peptides: Analysis, Synthesis, Biology. Volume 2: Special Methods in Peptide Synthesis, Part A"; Gross, E., Meienhofer, J. Eds.; Academic Press: New York, 1980; pp. 3–284). Solvents were HPLC grade. DMF was purged with nitrogen for 15–30 minutes prior to use. Couplings were done by treatment with 6.7 molar excess of the amino acid in the presence of an equivalent amount of DIPCDI for 2 hours in a 1:1 mixture of $CH_2Cl_2$ and DMF. Asn and Gln were coupled in the presence of 1.5 equivalents of 1-hydroxybenzotriazole. The following amino acids were double coupled: Asn, Gln, Ile, Val, and Nle. Unreacted amino groups were capped by treatment with 0.3 M 1-acetylimidazole in DMF before proceeding with the next synthetic cycle. The Boc groups were removed by treatment with a solution of 45% TFA and 2.5% anisole in dichloromethane.

Boc-Bln-OH was coupled to 2.00g MBHA-resin containing approximately 0.3 mmol of amino groups per gram of resin. The procedure for coupling and capping is carried out in accordance with Schedule A.

| Schedule A | |
|---|---|
| Reagent | Mixing Time (Min:Sec) |
| 1. CH$_2$Cl$_2$ (5 times) | 0:15 |
| 2. CH$_2$Cl$_2$/DMF (1:1) | 1:30 |
| 3. DIPCDI in CH$_2$Cl$_2$ + Boc-amino acid in DMF | 110:00 |
| 4. CH$_2$Cl$_2$/DMF (1:1) (2 times) | 0:15 |
| 5. CH$_2$Cl$_2$ (5 times) | 0:15 |
| 6. DMF | 0:15 |
| 7. 1-Acetylimidazole in DMF | 60:00 |
| 8. DMF (2 times) | 0:15 |

The procedure for removal of the Boc group (deblocking) after each coupling is carried out as set forth in Schedule B.

| Schedule B | |
|---|---|
| Reagent | Mixing Time (Min:Sec) |
| 1. CH$_2$Cl$_2$ (4 times) | 0:15 |
| 2. 40% TFA/2.5% Anisole in CH$_2$Cl$_2$ | 1:00 |
| 3. 40% TFA/2.5% Anisole in CH$_2$Cl$_2$ | 20:00 |
| 4. CH$_2$Cl$_2$ (2 times) | 0:15 |
| 5. 50% DMF/50% CH$_2$Cl$_2$ (3 times) | 0:15 |
| 6. CH$_2$Cl$_2$ (2 times) | 0:15 |
| 7. 10% DIPEA in CH$_2$Cl$_2$ (3 times) | 0:15 |
| 8. CH$_2$Cl$_2$ (5 times) | 0:15 |

After completing the sequential addition of all of the amino acids, the resin bound peptide is dried under vacuum to provide 3.73 g of crude, resin-bound peptide. A 2.01 g portion of the resin-bound peptide was cleaved from the resin by treatment with 10 mL of anhydrous hydrogen fluoride (distilled from cobalt (III) fluoride), 1 mL of anisole and 1 ml of dimethyl sulfide per gram of resin for 30–45 min at 0° C. The HF and volatile organics were removed by vacuum distillation and the residue dried overnight in a vacuum desiccator. The free peptide was precipitated with diethyl ether, extracted with 50% acetic acid, concentrated under reduced pressure and lyophilized to provide 925 mg of crude peptide.

The crude peptide was purified by semi-preparative HPLC. The crude peptide was dissolved into water containing 0.1% TFA and approximately 10–50 mg was loaded onto a 1.0×25 cm Vydac C$_{18}$, 5$\mu$, 300A HPLC column (catalog number 218TP510). The column was eluted at a flow rate of 2.0–2.5 ml/min with a solvent system consisting of water containing 0.1% TFA (Solvent A) and 80% acetonitrile in water containing 0.1% TFA (Solvent B) in a linear gradient from 30% solvent B to 60% solvent B over 60 minutes. The eluent was monitored using a UV detector set at 220nm and the desired peak was collected. The fractions from several such runs were combined, lyophilized, and repurified as above when necessary. A total of 3.1 mg of pure peptide was obtained from 300 mg of the crude product.

The final product was shown to be homogeneous by analytical HPLC in two different solvent systems; thin layer chromatography (TLC); and amino acid analysis.

EXAMPLE 2

Preparation of [Asp$^8$,Nle$^{27}$]-hGRF(1–31)—NH$_2$

The synthesis of [Asp$^8$,Nle$^{27}$]-hGRF(1–31)—NH$_2$ was carried out as described in Example 1 beginning with 2.00 g of MBHA-resin. The yield of crude, resin-bound peptide after completion of the synthesis cycles was 3.01 g. A 2.00 g portion of the resin-bound peptide was cleaved from the resin as described in Example 1 to provide 440 mg of the crude analog. HPLC purification of 150 mg of the crude peptide as set forth in Example 1 provided 3.0 mg of the pure analog. The peptide was judged to be homogeneous by analytical HPLC; TLC; and amino acid analyses.

EXAMPLE 3

Preparation of [Asn$^{25}$,Nle$^{27}$]-hGRF(1–31)—NH$_2$

The synthesis of [Asn$^{25}$,Nle$^{27}$]-hGRF(1–31)—NH$_2$ was carried out as described in Example 1 beginning with 2.13 g of MBHA-resin. The yield of crude, resin-bound peptide after completion of the synthesis cycles was 3.34 g. A 1.57 g portion of the resin-bound peptide was cleaved from the resin as described in Example 1 to provide 250 mg of the crude analog. HPLC purification of 250 mg of the crude peptide as set forth in Example 1 provided 5.2 mg of the pure analog. The peptide was judged to be homogeneous by analytical HPLC; TLC; and amino acid analyses.

EXAMPLE 4

Preparation of [Asn$^3$,Asp$^8$,Nle$^{27}$]-hGRF(1–31)—NH$_2$

The synthesis of [Asn$^{25}$,Nle$^{27}$]-hGRF(1–31)—NH$_2$ was carried out as described in Example 1 beginning with 1.04 g of MBHA-resin. The yield of crude, resin-bound peptide after completion of the synthesis cycles was 1.61 g. A 1.60 g portion of the resin-bound peptide was cleaved from the resin as described in Example 1 to provide 681 mg of the crude analog. HPLC purification of 25.0 mg of the crude peptide as set forth in Example 1 provided 1.0 mg of the pure analog. The peptide was judged to be homogeneous by analytical HPLC; TLC; and amino acid analyses.

EXAMPLE 5

Preparation of [Asn$^3$,Asn$^{25}$,Nle$^{27}$]-hGRF(1-31)—NH$_2$

The synthesis of [Asn$^3$,Asn$^{25}$,Nle$^{27}$]-hGRF(1-31)—NH$_2$ was carried out as described in Example 1 beginning with 2.00 g of MBHA-resin. The yield of crude, resin-bound peptide after completion of the synthesis cycles was 3.88 g. A 2.01 g portion of the resin-bound peptide was cleaved from the resin as described in Example 1 to provide 585 mg of the crude analog. HPLC purification of 150 mg of the crude peptide as set forth in Example 1 provided 5.0 mg of the pure analog. The peptide was judged to be homogeneous by analytical HPLC; TLC; and amino acid analyses.

EXAMPLE 6

Preparation of [Asp$^8$,Asn$^{25}$,Nle$^{27}$]-hGRF(1-31)—NH$_2$

The synthesis of [Asp$^8$,Asn$^{25}$,Nle$^{27}$]-hGRF(1-31)—NH$_2$ was carried out as described in Example 1 beginning with 2.51 g of MBHA-resin. The yield of crude, resin-bound peptide after completion of the synthesis cycles was 4.30 g. A 2.13 g portion of the resin-bound peptide was cleaved from the resin as described in Example 1 to provide 850 mg of the crude analog. HPLC purification of 310 mg of the crude peptide as set forth in Example 1 provided 8.0 mg of the pure analog. The peptide was judged to be homogeneous by analytical HPLC; TLC; and amino acid analyses.

EXAMPLE 7

Preparation of [Asn$^3$,Asp$^8$,Asn$^{25}$,Nle$^{27}$]-hGRF(1-31)—NH$_2$

The synthesis of [Asn$^3$,Asp$^8$,Asn$^{25}$,Nle$^{27}$]-hGRF(1-31)—NH$_2$ was carried out as described in Example 1 beginning with 2.00 g of MBHA-resin. The yield of crude, resin-bound peptide after completion of the synthesis cycles was 3.54 g. A 1.51 g portion of the resin-bound peptide was cleaved from the resin as described in Example 1 to provide 625 mg of the crude analog. HPLC purification of 185 mg of the crude peptide as set forth in Example 1 provided 5.0 mg of the pure analog. The peptide was judged to be homogeneous by analytical HPLC; TLC; and amino acid analyses.

EXAMPLE 8

Bioassay of hGRF Analogs

The biological activity of the synthesized hGRF analogs of the present invention was compared with that of synthetic hGRF(1-44)—NH$_2$ which is comparable to the natural hGRF(1-44)—NH$_2$. Biological activity of the synthetic hGRF(1-44)—NH$_2$ was identical to the natural hGRF(1-44)—NH$_2$ which was isolated from a human pancreatic tumor of an individual suffering from acromegaly (Salk Institute standard hGRF-NH$_2$ (NL-A-10).4). The assay for biological activity, which is based on the ability to stimulate release of growth hormone in rat pituitary cells in tissue culture, has been described in detail (Culler, M. D.; Kenjo, T.: Obara, N.; Arimuar, A., Stimulation of cAMP. Accumulation by Human Pancreatic GH-Releasing Factor-(1-44). *Am. J. Physiol.* 1984, 247 (Endocrinol.Metab.10), E609–E615.

ALLFIT, the 4-parameter logistic curve fitting program available from the Biomedical Computer Technology Information Center, Vanderbilt Medical Center, Nashville TN, was used to determine ED$_{50}$ and maximal stimulated values from the data. In several instances, the amount of GH released reached a maximum value and decreased with further increasing doses of the hGRF analogs. To simplify the data analysis, these values were not used in the calculations. The actual data points are shown in Table 1. The calculated maximal responses, the doses of the analog required to release the amount of GH released at the ED$_{50}$ of the standard (hGRF) and the potencies of the analogs relative to hGRF, are given in Table 2. Generally all novel analogs were fully active and were able to stimulate the release of growth hormone with maximal values of GH release being within 80% of the value for natural hGRF. There was a wide distribution of potencies as seen by the shift in the dose-response curves of the analogs.

Referring to Table 1, GRF analogs [Nle$^{27}$]-hGRF(1-31)NH$_2$, Asn$^3$, Nle$^{27}$]-hGRF(1-31)—NH$_2$, Asp$^8$, Nle$^{27}$]-hGRF(1-31)—NH$_2$, [Asn$^{25}$, Nle$^{27}$]-hGRF(1-31)NH$_2$, [Asn$^3$, Asn$^{25}$, Nle$^{27}$]-hGRF(1-31)—NH$_2$, and [Asp$^8$, Asn$^{25}$, Nle$^{27}$]-hGRF(1-31)—NH$_2$ induced GH release in dosages comparable to those for native hGRF while analogs [Asn$^3$, Asp$^8$, Nle$^{27}$]-hGRF(1-31)—NH$_2$; and [Asn$^3$, Asp$^8$, Asn$^{25}$, Nle$^{27}$]-hGRF(1-31)—NH$_2$ did not induce GH release at dosages comparable to native hGRF. Surprisingly, the data indicates that some analogs of the present invention having substitutions at positions 3, 8, and 25 retain high levels of bioactivity while others retain only low levels of bioactivity. While not wishing to be bound by theory, it is believed that the nature of the residues at these positions is important for determining receptor binding affinities and therefore bioactivity.

Referring to Table 2, the data surprisingly shows that the potency of the analogs of the present invention varies greatly. Potency of 82 and 76% were found for analogs [Asp$^8$,Nle$^{27}$]-hGRF(1-31)—NH$_2$ and [Asp$^8$,Asn$^{25}$, Nle$^{27}$]-hGRF(1-31)—NH$_2$, respectively. In contrast, potency of only 3 and 5% was found for analogs, [Asn$^3$,Asp$^8$,Nle$^{27}$]-hGRF(1-31)—NH$_2$ and [Asn$^3$,Asp$^8$,Asn$^{25}$,Nle$^{27}$]-hGRF(1-31)—NH$_2$, respectively. The analog [Asn$^{25}$,Nle$^{27}$]-hGRF(1-31)—NH$_2$ was 2.7 times more potent than hGRF(1-44)—NH$_2$ on a molar basis.

Obviously many modifications and variations of the present invention are possible in light of the above teachings. It is therefore to be understood that within the scope of the appended claims the invention may be practiced otherwise than as specifically described.

TABLE 1

| | GH Release from Cultured Pituitary Cells Stimulated by the hGRF Analogs | |
|---|---|---|
| Analog | Dose (M) | GH Released ($\mu$g/mL; mean $\pm$ (S.E.)) |
| — | — | 0.69 (0.05) |
| hGRF | $1 \times 10^{-11}$ | 0.73 (0.03) |
| | $1 \times 10^{-10}$ | 1.16 (0.04) |
| | $1 \times 10^{-9}$ | 2.84 (0.12) |
| | $1 \times 10^{-8}$ | 3.44 (0.23) |
| | $1 \times 10^{-7}$ | 3.17 (0.12) |
| | $1 \times 10^{-6}$ | 2.81 (0.13) |
| [Nle$^{27}$]- | $1 \times 10^{-11}$ | 0.85 (0.03) |

TABLE 1-continued
GH Release from Cultured Pituitary Cells Stimulated by the hGRF Analogs

| Analog | Dose (M) | GH Released (μg/mL; mean ± (S.E.)) |
|---|---|---|
| | $1 \times 10^{-10}$ | 1.93 (0.10) |
| | $1 \times 10^{-9}$ | 3.16 (0.12) |
| | $1 \times 10^{-8}$ | 3.11 (0.23) |
| | $1 \times 10^{-7}$ | 2.78 (0.09) |
| | $1 \times 10^{-6}$ | 2.89 (0.08) |
| [Asn$^3$,Nle$^{27}$]- | $1 \times 10^{-11}$ | 0.67 (0.08) |
| | $1 \times 10^{-10}$ | 0.97 (0.01) |
| | $1 \times 10^{-9}$ | 2.40 (0.06) |
| | $1 \times 10^{-8}$ | 2.90 (0.12) |
| | $1 \times 10^{-7}$ | 3.05 (0.09) |
| | $1 \times 10^{-6}$ | 3.22 (0.16) |
| [Asp$^8$,Nle$^{27}$]- | $1 \times 10^{-11}$ | 0.61 (0.03) |
| | $1 \times 10^{-10}$ | 1.18 (0.10) |
| | $1 \times 10^{-9}$ | 2.69 (0.12) |
| | $1 \times 10^{-8}$ | 3.59 (0.17) |
| | $1 \times 10^{-7}$ | 3.52 (0.22) |
| | $1 \times 10^{-6}$ | 3.17 (0.24) |
| [Asn$^{25}$,Nle$^{27}$]- | $1 \times 10^{-11}$ | 0.72 (0.05) |
| | $1 \times 10^{-10}$ | 1.84 (0.06) |
| | $1 \times 10^{-9}$ | 3.12 (0.15) |
| | $1 \times 10^{-8}$ | 3.10 (0.12) |
| | $1 \times 10^{-7}$ | 3.22 (0.09) |
| | $1 \times 10^{-6}$ | 3.22 (0.24) |
| [Asn$^3$,Asp$^8$,Nle$^{27}$]- | $1 \times 10^{-11}$ | 0.65 (0.04) |
| | $1 \times 10^{-10}$ | 0.58 (0.04) |
| | $1 \times 10^{-9}$ | 1.04 (0.05) |
| | $1 \times 10^{-8}$ | 2.27 (0.07) |
| | $1 \times 10^{-7}$ | 3.30 (0.27) |
| | $1 \times 10^{-6}$ | 2.74 (0.19) |
| [Asn$^3$,Asn$^{25}$,Nle$^{27}$]- | $1 \times 10^{-11}$ | 0.65 (0.03) |
| | $1 \times 10^{-10}$ | 0.81 (0.06) |
| | $1 \times 10^{-9}$ | 1.58 (0.07) |
| | $1 \times 10^{-8}$ | 3.21 (0.13) |
| | $1 \times 10^{-7}$ | 3.30 (0.08) |
| | $1 \times 10^{-6}$ | 2.96 (0.11) |
| [Asp$^8$,Asn$^{25}$,Nle$^{27}$]- | $1 \times 10^{-11}$ | 0.74 (0.09) |
| | $1 \times 10^{-10}$ | 0.96 (0.07) |
| | $1 \times 10^{-9}$ | 2.59 (0.17) |
| | $1 \times 10^{-8}$ | 2.86 (0.08) |
| | $1 \times 10^{-7}$ | 2.93 (0.17) |
| | $1 \times 10^{-6}$ | 2.86 (0.07) |
| [Asn$^3$,Asp$^8$,Asn$^{25}$,Nle$^{27}$]- | $1 \times 10^{-11}$ | 0.60 (0.02) |
| | $1 \times 10^{-10}$ | 0.61 (0.05) |
| | $1 \times 10^{-9}$ | 0.75 (0.01) |
| | $1 \times 10^{-8}$ | 1.88 (0.07) |
| | $1 \times 10^{-7}$ | 2.94 (0.11) |
| | $1 \times 10^{-6}$ | 3.12 (0.12) |

S.E. = standard error

TABLE 2
Bioactivity of the hGRF Analogs from Curves Generated by ALLFIT

| -hGRF(1-31)-NH$_2$ Analog | Maximum GH Released (μg/mL) | Relative Maximum Activity (% of hGRF) | Dose Needed to Release 2.01 μg/ml of GH$^a$ (nM) | Potency$^b$ (%) |
|---|---|---|---|---|
| hGRF(1-44)-NH$_2$ | 3.31 | 100 | 0.32 | 100 |
| [Nle$^{27}$] | 3.16 | 95 | 0.11 | 291 |
| [Asn$^3$,Nle$^{27}$] | 3.09 | 93 | 0.58 | 55 |
| [Asp$^8$,Nle$^{27}$] | 3.60 | 109 | 0.39 | 82 |
| [Asn$^{25}$,Nle$^{27}$] | 3.18 | 96 | 0.12 | 267 |
| [Asn$^3$,Asp$^8$,Nle$^{27}$] | 3.53 | 107 | 6.74 | 5 |
| [Asn$^3$,Asn$^{25}$,Nle$^{27}$] | 3.33 | 101 | 1.54 | 21 |
| [Asp$^8$,Asn$^{25}$,Nle$^{27}$] | 2.89 | 87 | 0.42 | 76 |
| [Asn$^3$,Asp$^8$,Asn$^{25}$,Nle$^{27}$] | 3.11 | 94 | 12.05 | 3 |

$^a$ED$_{50}$ Value for hGRF
$^b$(ED$_{50}$ of hGRF)/(Dose required to give same response as ED$_{50}$ of hGRF).
nM = nanomolar

I claim:

1. A Human Growth Hormone-Releasing Factor (hGRF) analog having a sequence selected from the group consisting
[Asp$^8$, Nle$^{27}$]-hGRF(1-31)—NH$_2$;
[Asn$^{25}$, Nle$^{27}$]-hGRF(1-31)—NH$_2$;
[Asn$^3$, Asn$^{25}$, Nle$^{27}$]-hGRF(1-31)—NH$_2$;
[Asp$^8$, Asn$^{25}$, Nle$^{27}$]-hGRF(1-31)—NH$_2$;
[Asn$^3$, Asp$^8$, Nle$^{27}$]-hGRF(1-31)—NH$_2$; and
[Asn$^3$, Asp$^8$, Asn$^{25}$, Nle$^{27}$]-hGRF(1-31)—NH$_2$.

2. The hGRF analog of claim 1 having a sequence selected from the group consisting of:
[Asp$^8$, Nle$^{27}$]-hGRF(1-31)—NH$_2$;
[Asn$^{25}$, Nle$^{27}$]-hGRF(1-31)—NH$_2$;
[Asn$^3$, Asn$^{25}$, Nle$^{27}$]-hGRF(1-31)—NH$_2$; and
[Asp$^8$, Asn$^{25}$, Nle$^{27}$]-hGRF(1-31)—NH$_2$.

3. A method for stimulating the release of growth hormone (GH) in animals, comprising:
administering to said animals an amount of a human growth hormone-releasing factor (hGRF) analog sufficient to stimulate the release of growth hormone (GH), the hGRF analog having a sequence selected from the group consisting of:
[Asp$^8$, Nle$^{27}$]=hGRF(1-31)—NH$_2$;
[Asn$^{25}$, Nle$^{27}$]-hGRF(1-31)—NH$_2$;
[Asn$^3$, Asn$^{25}$, Nle$^{27}$]-hGRF(1-31)—NH$_2$;
[Asp$^8$ Asn$^{25}$, Nle$^{27}$]-hGRF(1-31)—NH$_2$;
[Asn$^3$, Asn$^8$, Nle$^{27}$]-hGRF(1-31)—NH$_2$; and
[Asn$^3$, Asp$^8$, Asn$^{25}$, Nle$^{27}$]-hGRF(1-31)—NH$_2$.

4. The method of claim 3 wherein the hGRF analog has a sequence selected from the group consisting of:
[Asp$^8$ Nle$^{27}$]-hGRF(1-31)—NH$_2$;
[Asn$^{25}$, Nle$^{27}$]-hGRF(1-31)—NH$_2$;
[Asn$^3$, Asn$^{25}$, Nle$^{27}$]-hG(1-31)—NH$_2$; and
[Asp$^8$, Asn$^{25}$, Nle$^{27}$]-hGRF(1-31)—NH$_2$.

5. The method of claim 3 wherein the hGRF analog is administered in dosages of from about 0.05–100 μg/kg of body weight/day.

6. The method of claim 3 wherein the hGRF analog is administered parenterally.

7. The method of claim 6 wherein the hGRF analog is administered using an implant, said implant further comprising:
a biocompatible and the hGRF analog compatible implant material; and
an amount of the hGRF analog sufficient to stimulate the release of GH.

8. The method of claim 6 wherein the hGRF analog is administered in an injectable formulation, said injectable formulation further comprising:
a biocompatible and the hGRF analog compatible carrier; and
an amount of the hGRF analog sufficient to stimulate the release of GH.

9. The method of claim 3 wherein said animals are selected from the group consisting of cattle and sheep.

10. A composition for stimulating the release of growth hormone (GH) in animals. comprising:
a pharmaceutically acceptable carrier; and an amount of a human growth hormone-releasing factor (hGRF) analog sufficient to stimulate the release of GH, the hGRF analog having a sequence selected from the group consisting of:
[Asp$^8$, Nle$^{27}$]-hGRF(1-31)—NH$_2$;
[Asn$^{25}$, Nle$^{27}$]-hGRF(1-31)—NH$_2$;
[Asn$^3$, Asn$^{25}$, Nle$^{27}$]-hGRF(1-31)—NH$_2$;
[Asp$^8$, Asn$^{25}$, Nle$^{27}$]-hGRF(1-31)—NH$_2$;

[Asn³, Asp⁸, Nle²⁷]-hGRF(1-31)—NH₂; and
[Asn³, Asp⁸, Asn²⁵, Nle²⁷]-hGRF(1-31)—NH₂.

11. The composition of claim 10 wherein the hGRF analog has a sequence selected from the group consisting of:
[Asp⁸, Nle²⁷]-hGRF(1-31)—NH₂;
[Asn²⁵ Nle²⁷]-hGRF(1-31)—NH₂;
[Asn³, Asn²⁵, Nle²⁷]-hGRF(1-31)—NH₂; and
[Asp⁸ Asn²⁵, Nle²⁷]-hGRF(1-31)—NH₂.

12. The composition of claim 10 containing the hGRF analog in dosages of from about 0.05-100 μg/kg of body weight/day.

13. The composition of claim 10 in a form suitable for parenteral administration.

14. The composition of claim 13 in the form of an implant, said implant further comprising:
   a biocompatible and the hGRF analog compatible implant material; and
   an amount of the hGRF analog sufficient to stimulate the release of GH.

15. The composition of claim 13 in the form of an injectable formulation, said injectable formulation further comprising:
   a biocompatible and the hGRF analog compatible carrier; and
   an amount of the hGRF analog sufficient to stimulate the release of GH.

* * * * *

Notice of Adverse Decisions in Interference

In Interference No. 102,286, involving Patent No. 4,801,456, K. A. Drengler, GROWTH HORMONE-RELEASING FACTOR ANALOGS, final judgement adverse to the patentee was rendered Sept. 11, 1990, as to claims 1-15.

*[Official Gazette October 23, 1990]*